United States Patent [19]
Hagen et al.

[11] 4,163,020
[45] Jul. 31, 1979

[54] 2-TRICHLOROMETHYL-4-NITROBEN-ZENESULFENIC ACID DERIVATIVES

[75] Inventors: Helmut Hagen, Frankenthal; Wolfgang Reuther, Ziegelhausen; Ernst-Heinrich Pommer, Limburgerhof; Helmut Fleig, Mannheim, all of Fed. Rep. of Germany

[73] Assignee: BASF Aktiengesellschaft, Fed. Rep. of Germany

[21] Appl. No.: 899,523

[22] Filed: Apr. 24, 1978

[30] Foreign Application Priority Data

May 14, 1977 [DE] Fed. Rep. of Germany ....... 2721917

[51] Int. Cl.$^2$ .................. C07C 161/02; C07C 145/00
[52] U.S. Cl. .............................. 260/454; 260/543 H
[58] Field of Search ........................... 260/454, 543 H

[56] References Cited

U.S. PATENT DOCUMENTS 3,980,689  9/1976  Pelosi, Jr. .............................. 260/454

*Primary Examiner*—Natalie Trousof
*Assistant Examiner*—Robert C. Whittenbaugh
*Attorney, Agent, or Firm*—Keil & Witherspoon

[57] ABSTRACT

New 2-trichloromethyl-4-nitrobenzenesulfenic acid derivatives having a fungicidal and bactericidal action, agents for combatting fungi and bacteria containing these compounds as active ingredients, processes for combatting fungi and bacteria with these active ingredients, and processes for their manufacture. Of particular interest are 2-trichloromethyl-4-nitrobenzenesulfenic acid chloride and 2-trichloromethyl-4-nitrophenyl thiocyanate.

3 Claims, No Drawings

2-TRICHLOROMETHYL-4-NITROBENZENESULFENIC ACID DERIVATIVES

The present invention relates to new 2-trichloromethyl-4-nitrobenzenesulfenic acid derivatives having a microbicidal, fungicidal and bactericidal action, microbicides containing these compounds as active ingredients, processes for combatting fungi and bacteria with these compounds, and processes for their manufacture.

It is known to use N-trichloromethylthiophthalimide (Chemical Week, 1972, June 21, p. 63) and 2-thiocyanomethylthiobenzothiazole (Farm Chemicals Handbook, 1976, p. D43) as fungicides. However, their action is unsatisfactory.

It is an object of the present invention to provide new active ingredients and microbicides having an improved action.

We have found that this object is achieved by means of 2-trichloromethyl-4-nitrobenzenesulfenic acid derivatives of the formula

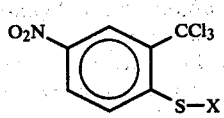

where X denotes —Cl or —CN which have a better fungicidal action than the abovementioned prior art active ingredients. The new active ingredients are particularly suitable for protecting various materials against degradation or destruction by bacteria and fungi; furthermore, they have an algicidal action.

Examples of materials which may be preserved with the new active ingredients, or to which they may impart a microbicidal effect, are glues and adhesives, plastics dispersions, emulsion paints, sealing compounds, paper, textiles, leather, raw hides, plastics, especially soft PVC, rubber products and wood. The compounds are also suitable as microbicidally active additives in cleaning agents and disinfectants, as fungus-resistant additives for moisture-proof paints and anti-slime agents in the paper industry.

Examples of microorganisms which may be controlled with the new compounds are *Staphylococcus aureus, Escherichia coli, Pseudomonas fluorescens, Ps.aeruginosa, Proteus vulgaris, Klebsiella aerogenes, Citrobacter freundii, Achromobacter mucosus, Aerobacter aerogenes, Bacterium subtilis, B.mycoides, Lactobacillus plantarum;*

*Desulfovibrio desulfuricans, Serratia marcescens, Chaetomium globosum, Ch. alba, Aspergillus terrus, A.niger, A.flavus, A.versicolor, Streptomyces albus, Penicillium glaucum, P.citrinum, P.luteum, P.funiculosum, Trichoderma viride, Oidium lactis, Candida albicans, Saccharomyces cerevisiae, Pullularia pullulans, Sclerophoma pityophila, Cladosporium herbarum, Cl.resinae, Alternaria spec., Humicola grisea, Petriella setifera, Glenospora graphii, Trichurus spiralis, Phoma violacea, Coniophora cerebella, Merulius lacrymans, Lenzites trabea, L.abietina, Trametes versicolor, and Armillaria mellea.*

Trichloromethyl-4-nitrobenzenesulfenic acid chloride may for instance be prepared by chlorination of 5-nitrobenzo-1,2-dithio-3-thione in an inert solvent and at from −20° to +100° C., preferably from 0° to 50° C. Examples of inert solvents are chlorinated hydrocarbons such as carbon tetrachloride, chloroform, dichloroethane, etc.

The reaction may be described by the following equation:

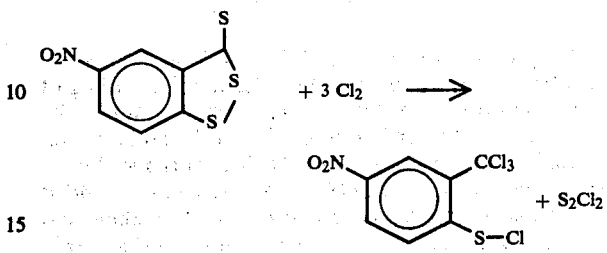

The 5-nitrobenzo-1,2-dithio-3-thione used as starting compound may readily be prepared by the process disclosed in German Laid-Open Application DOS No. 2,460,783, and as described in the following method.

51.5 g of 2-chloro-5-nitrobenzyl chloride is heated with 24 g of sulfur in 500 ml of methanol for 30 minutes at 50° C. Over a period of 1 hour, 50.5 g of triethylamine is added and the reaction mixture heated for 20 hours at 65° C. After the mixture has cooled, th precipitated solid is suction filtered and washed with water. There is obtained 50.5 g (89% of theory) of 5-nitrobenz-1,2-dithio-3-thione. Melting point: 172°–173° C. (decomposes).

The preparation of 2-trichloromethyl-4-nitrophenyl thiocyanate

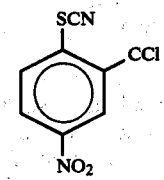

may for instance be carried out by reaction of 2-trichloromethyl-4-nitrobenzenesulfenic acid chloride with sodium cyanide or potassium cyanide.

The reaction may be described by the following equation:

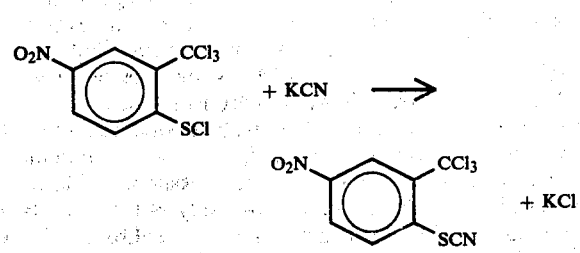

The reaction is expediently carried out in a solvent, e.g., diethyl ether, tetrahydrofuran, dioxane, dimethylformamide, glacial acetic acid or a mixture of such solvents, and at from 0° to 120° C., preferably from 20° to 80° C.

The preparation of the new active ingredients is illustrated in the following examples.

EXAMPLE 1

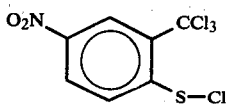

115 g of 5-nitrobenzo-1,2-dithio-3-thione is dispersed in 1,000 ml of carbon tetrachloride; at 10° C., 150 g of chlorine is passed in. The reaction mixture is stirred for 12 hours at room temperature (25° C.). The solvent and sulfur chloride are then distilled off under reduced pressure from a waterpump. 400 ml of diethyl ether is added to the residue and filtration carried out. The ether solution is concentrated and distilled in vacuo. At 156°–160° C./1 mm Hg, 128 g (83% of theory) of 2-trichloromethyl-4-nitrobenzenesulfenic acid chloride is obtained. The compound melts at 56°–57° C. (from ligroin).

EXAMPLE 2

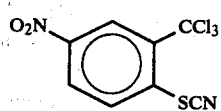

At 10° to 15° C., 13 g of potassium cyanide is dissolved in 100 ml of glacial acetic acid. At 10° C., a solution of 61.4 g of 2-trichloromethyl-4-nitrobenzenesulfenic acid chloride in 200 ml of diethyl ether is added to the solution. The mixture is stirred for 2 hours at 10° C. and for 5 hours at room temperature. The precipitated potassium chloride is filtred off, the solvent is distilled off, and the residue is recyrstallized from petroleum ether. There is obtained 53 g (89% of theory) of 2-trichloromethyl-4-nitrophenyl thiocyanate; m.p.: 72° C.

The new active ingredients are used in the form of formulations. The formulations, such as solution, emulsions, suspensions, wettable powders, dusts, pastes and granules, are applied in conventional manner, e.g., coating, impregnating and bating. The formulations generally contain from 0.1 to 95, preferably from 0.5 to 90, wt% of active ingredient. Depending on the effect desired, the application rates are from 0.001 to 5% (wt%), based on the weight of the material to be protected; preferably, the rates are from 0.01 to 3%.

For the preparation of emulsions, pastes and oil dispersions, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepared emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possible solvent or oil.

Examples of surfactants are: alkali metal, alkaline earth metal and ammonium salts or ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

The following list of bactericides and fungicides with which the active ingredients may be combined is intended to illustrate, and not restrict, the mixture possibilities. As a result of combination with other active ingredients, the microbicidal spectrum of action is often widened; with a number of these microbicide compositions, synergistic effects also occur, i.e., the microbicidal action of the combination product is greater than the sum of the actions of its components.

Organotin compounds, such as tributyltin oxide and triphenyltin benzoate
2-Bromo-2-nitro-1,3-propanediol
Methylenebisthiocyanate
Chloroethylenebisthiocyanate
Formaldehyde
Glutaraldehyde
Chloroacetamide
N-Methylol-chloroacetamide
Sodium and zinc dimethyldithiocarbamate
Tetramethylthiuramdisulfide
1,6-Bis-(4-chlorophenyldiguanido)-hexane
Alkyl-trimethyl-ammonium chloride
Alkyl-dimethyl-benzylammonium chloride
Cetylpyridinium chloride
Dodecyl-di-(aminoethyl)-glycine
o-Phenyl-phenol
p-Chloro-m-cresol
Chlorinated phenols
p-Hydroxybenzoate
Tetrachloroisophthalic acid dinitrile
Halogenated salicylanilides
α-Halobenzanilide
N-Cyclohexyl-N-methoxy-2,5-dimethylfuran-3-carboxylic acid amide
N,N-Dimethyl-N'-phenyl-(N-fluorodichloromethylthio)-sulfamide
N-Phenyl-N,N'-dimethyl-N'-fluorodichloromethylthiosulfonyldiamide
N-Trichloromethylthiophthalimide
N-Fluorodichloromethylthiophthalimide N-(1,1,2,2-Tetrachloroethylthio)-tetrahydrophthalimide
Methyl benzimidazole-2-carbamate
2-(Thiazolyl)-benzimidazole
2-Mercaptobenzothiazole The greater the extent to which the active ingredient is diluted, the more active is the compound. An active ingredient only achieving kill at a dilution ratio of 1:8,000 is therefore less effective than one achieving the same effect at a dilution ratio of 1:100,000.

| Active ingredient | Full bactericidal and fungicidal activity (kill) at dilution ratio of | | | |
|---|---|---|---|---|
| | Staphylococcus aureus | Escherichia coli | Pseudomonas fluorescens | Oidium lactis |
| 1 | 1: 40,000 | 1: 20,000 | 1: 20,000 | 1:200,000 |
| 2 | 1:100,000 | 1:100,000 | 1: 40,000 | 1:400,000 |
| 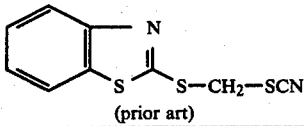 (prior art) | 1: 16,000 | 1: 8,000 | 1: 8,000 | 1: 40,000 |

2-Thiocyanomethylthiobenzothiazole
Benzisothiazolone
2,5-Dimethyltetrahydro-1,3,5-2H-thiadiazine-2-thione
Tris-(N-cyclohexyl-N-diazoniumdioxi)-aluminum The above active ingredients may be added to the compounds according to the invention in a ratio by weight of from 1:10 to 10:1.

The following examples demonstrate the effectiveness of the compounds

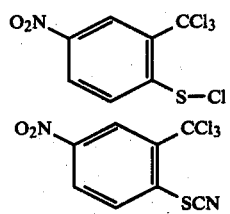

1

2 on fungi and bacteria.

EXAMPLE 3

Bacterial action on *Staphylococcus aureus, Escherichia coli* and *Pseudomonas fluorescens*, and fungicidal action on *Oidium lactis*

The kill rates for the first three bacteria were determined as follows. 5 ml of doubly concentrated nitrient broth was added to 5 ml of a dilution of the agents in water in sterile test tubes, and the whole mixed. The tubes were then inoculated by adding one drop of a 16 hour old nitrient Staphylococcus, Escherichia or Pseudomonas culture (diluted 1:10), and then incubated for 24 hours at 37° C. Samples were subsequently transferred from the tubes to bacteria culture media, which were then also incubated for 24 hours at 37° C. The dilution stage at which no bacterial growth takes place after the transfer of a sample to the culture medium is given as the kill rate. The test of the fungicidal action of the new compounds on Oidium lactis was carried out by adding the active ingredients in various amounts, graduated down to 1:1,000,000, to a nutrient solution (Sabourand nutrient solution) ideally suited for promoting the growth of fungi. 10 ml of the nutrient solutions treated in this manner was then inoculated, in test tubes, with spores of Oidium fungus. The tubes were kept for 5 days at 25° C. The dilution stage at which no more fungus growth was observed was determined by transferring samples to culture media.

EXAMPLE 4

Fungicidal action on *Aspergillus niger*

The active ingredients are added to a nutrient solution ideally suited for promoting the growth of the fungus *Aspergillus niger* in amounts of 100, 50, 25, 10, 5 and 1 parts by weight per million parts of nutrient solution. 20 ml of the nutrient solution treated in this manner is inoculated, in 100 ml glass flasks, with 0.3 mg of Aspergillus fungus spores. The flasks are heated for 120 hours at 36° C. and the extent of fungus spread (predominantly on the surface of the nutrient solution) is assessed.

0=no fungus growth, graduated down to 5=uncontrolled fungus growth (surface of nutrient solution completely covered by fungus).

| Active ingredient | Amount of active ingredient in nutrient Solution in ppm | | | | | |
|---|---|---|---|---|---|---|
| | 100 | 50 | 25 | 10 | 5 | 1 |
| 1 | 0 | 0 | 0 | 0 | 3 | 5 |
| 2 | 0 | 0 | 0 | 0 | 0 | 0 |
| 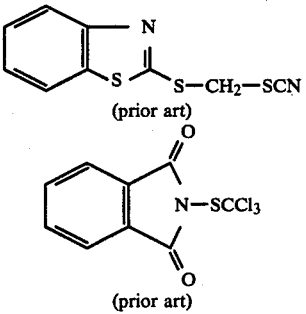 (prior art) | 0 | 3 | 3 | 5 | 5 | 5 |
| 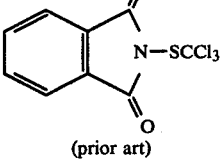 (prior art) | 0 | 1 | 1 | 3 | 5 | 5 |

EXAMPLE 5

90 parts by weight of compound 1 is mixed with 10 parts by weight of N-methylα-pyrrolidone. A mixture is obtained which is suitable for application in the form of very fine drops.

EXAMPLE 6

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 1 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.025 by weight of the active ingredient.

EXAMPLE 8

20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 2 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of watr, a spray liquid is obtained containing 0.1% by weight of the active ingredient.

EXAMPLE 10

3 parts by weight of compound 2 is intimately mixed with 97 parts by weight of particulate kaolin. A dust is obtained containing 3% by weight of the active ingredient.

EXAMPLE 11

30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 12 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 13

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

we claim:

1. A 2-trichloromethyl-4-nitrobenzenesulfenic acid derivative of the formula

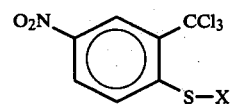

where X is —Cl or —CN.

2. 2-trichloromethyl-4-nitrobenzenesulfenic acid chloride.

3. 2-trichloromethyl-4-nitrophenyl thiocyanate.